US009759656B2

(12) United States Patent
Ito et al.

(10) Patent No.: US 9,759,656 B2
(45) Date of Patent: Sep. 12, 2017

(54) INSPECTION APPARATUS AND INSPECTION METHOD

(71) Applicants: SCREEN HOLDINGS CO., LTD., Kyoto-shi, Kyoto (JP); NATIONAL INSTITUTE OF ADVANCED INDUSTRIAL SCIENCE AND TECHNOLOGY, Tokyo (JP)

(72) Inventors: Akira Ito, Kyoto (JP); Hidetoshi Nakanishi, Kyoto (JP); Toshimitsu Mochizuki, Koriyama (JP); Hidetaka Takato, Koriyama (JP); Katsuhiko Shirasawa, Koriyama (JP)

(73) Assignees: SCREEN HOLDINGS CO., LTD., Kyoto (JP); NATIONAL INSTITUTE OF ADVANCED INDUSTRIAL SCIENCE AND TECHNOLOGY, Tokyo (JP)

( * ) Notice: Subject to any disclaimer, the term of this patent is extended or adjusted under 35 U.S.C. 154(b) by 0 days.

(21) Appl. No.: 15/428,372

(22) Filed: Feb. 9, 2017

(65) Prior Publication Data
US 2017/0234792 A1    Aug. 17, 2017

(30) Foreign Application Priority Data
Feb. 15, 2016    (JP) .................... 2016-026113

(51) Int. Cl.
*G01N 21/64*    (2006.01)
*G01N 21/84*    (2006.01)
(Continued)

(52) U.S. Cl.
CPC ......... *G01N 21/64* (2013.01); *G01N 21/8422* (2013.01); *H01L 21/67288* (2013.01); *H01L 23/12* (2013.01)

(58) Field of Classification Search
CPC ............... G01N 21/64; G01N 21/8422; H01L 21/67288; H01L 23/12
See application file for complete search history.

(56) References Cited

U.S. PATENT DOCUMENTS

| | | | |
|---|---|---|---|
| 2008/0165355 A1* | 7/2008 | Yasui ................ | G01N 21/3586 356/323 |
| 2009/0200472 A1* | 8/2009 | Gregory .................. | G01J 3/10 250/339.07 |

(Continued)

FOREIGN PATENT DOCUMENTS

| | | | |
|---|---|---|---|
| EP | 2574906 A1 | 4/2013 | |
| JP | 2013-038340 A | 2/2013 | |
| JP | EP 2679987 A1 * | 1/2014 | ......... G01N 21/9501 |

OTHER PUBLICATIONS

Shinsuke Miyajima, "Surface Passivation Films for Crystalline Silicon Solar Cells," J. Plasma Fusion Res. vol. 85, No. 2 (2009): 820-824 (w/concise explanation in English).

(Continued)

*Primary Examiner* — Mark R Gaworecki
(74) *Attorney, Agent, or Firm* — McDermott Will & Emery LLP

(57) ABSTRACT

The inspection apparatus includes: a stage that retains the inspection sample; a light irradiator that irradiates the inspection sample with light having a predetermined wavelength to cause the inspection sample to emit a terahertz wave; a detector that detects electric field intensity of the terahertz wave emitted from the inspection sample; and a comparator that compares the electric field intensity of the terahertz wave emitted from the inspection sample to an evaluation reference value. The evaluation reference value is a value (for example, 90% of a saturation value) smaller than an absolute value of the saturation value of the electric field intensity of the terahertz wave, the terahertz wave being (Continued)

generated by irradiating a reference sample, which is a reference of the inspection sample, with the light while different voltages are applied to the reference sample.

8 Claims, 11 Drawing Sheets

(51) Int. Cl.
*H01L 23/12* (2006.01)
*H01L 21/67* (2006.01)

(56) References Cited

U.S. PATENT DOCUMENTS

| | | | |
|---|---|---|---|
| 2011/0216312 A1* | 9/2011 | Matsumoto | G01N 21/9501 356/237.1 |
| 2013/0015368 A1* | 1/2013 | Nakanishi | G01N 21/3586 250/459.1 |
| 2013/0083319 A1 | 4/2013 | Nakanishi et al. | |
| 2015/0162872 A1* | 6/2015 | Nakanishi | G01R 31/2656 324/761.01 |
| 2015/0236642 A1* | 8/2015 | Nakanishi | H02S 50/15 356/237.1 |
| 2016/0109360 A1* | 4/2016 | Koizumi | G01N 21/35 250/338.1 |

OTHER PUBLICATIONS

Partial European Search Report issued in corresponding EP Patent Application No. 17155554.3, dated Jun. 22, 2017.

* cited by examiner

F I G. 4
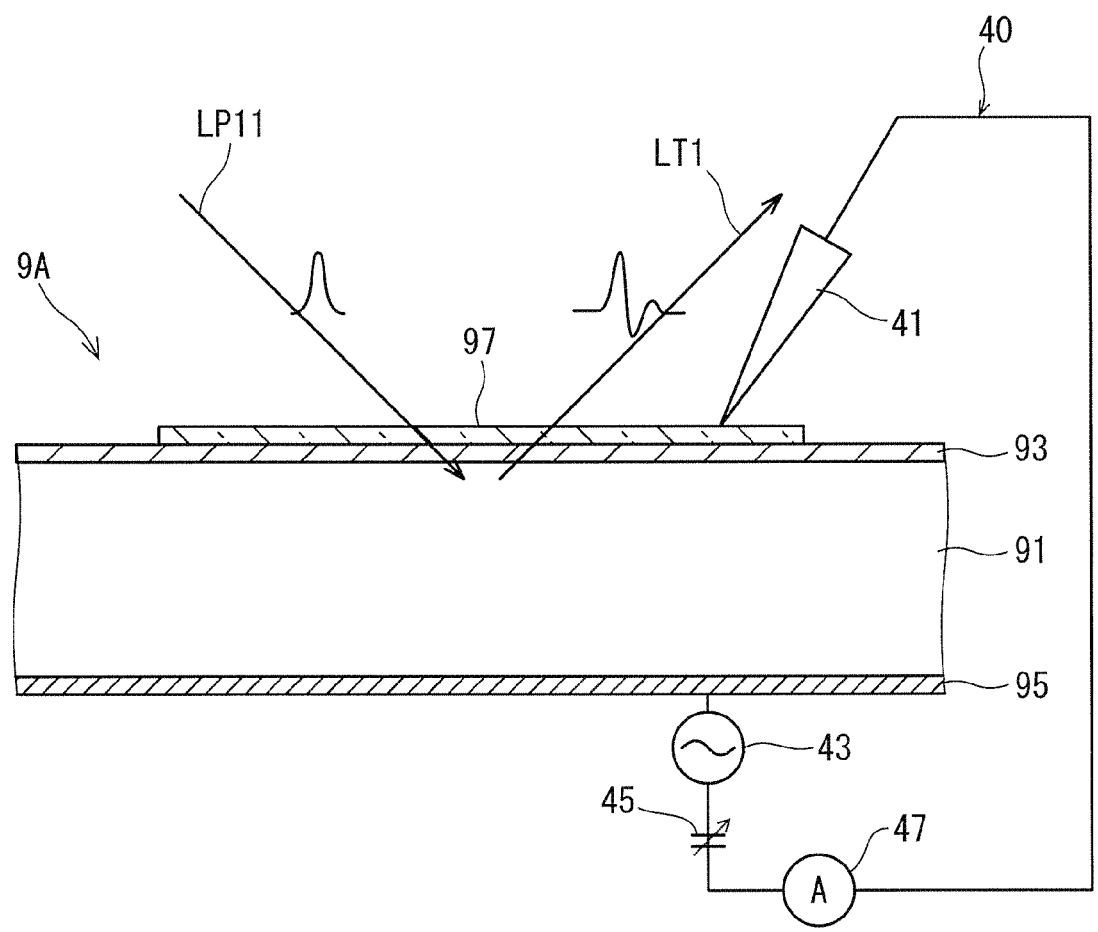

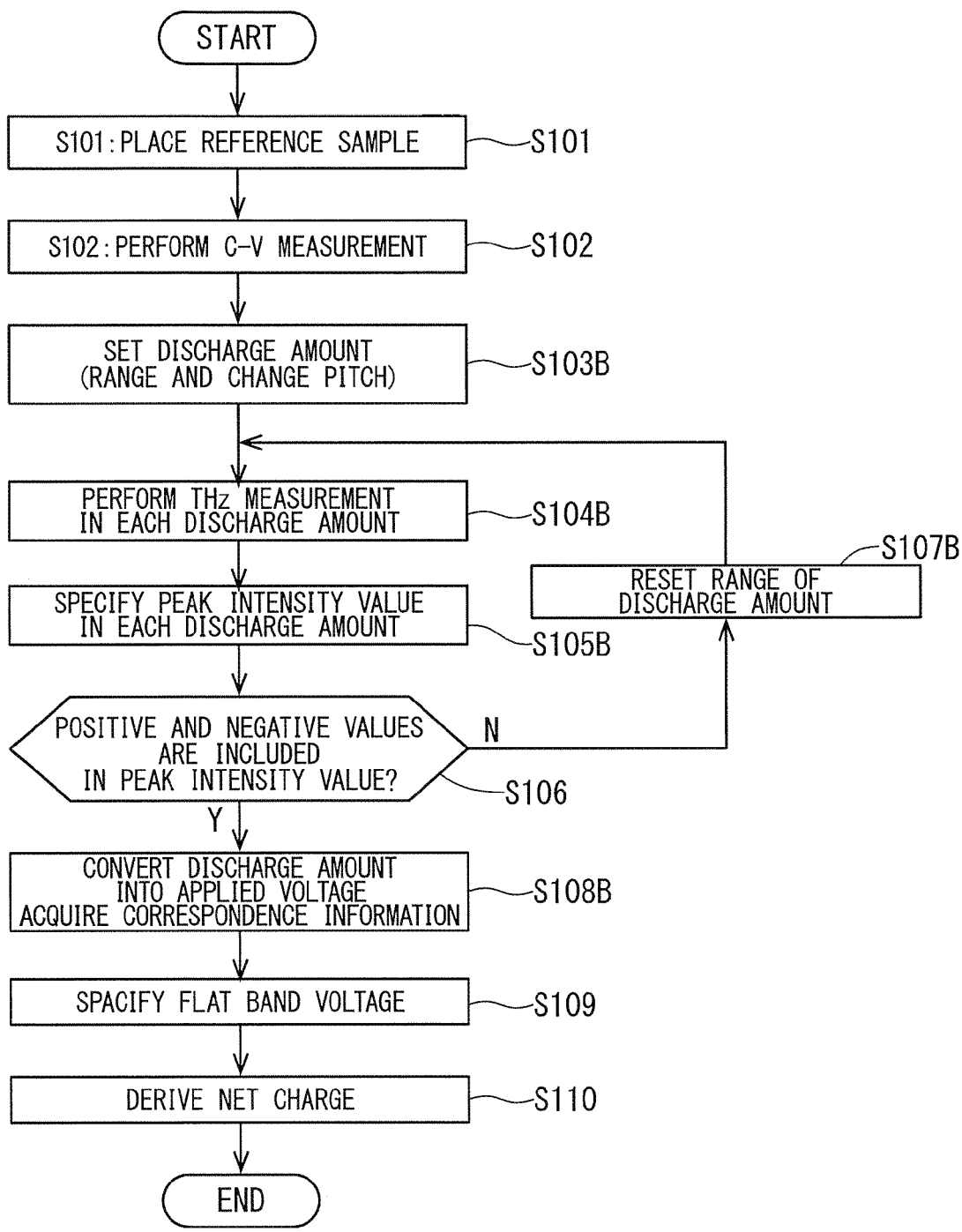
F I G. 1 1

INSPECTION APPARATUS AND INSPECTION METHOD

BACKGROUND OF THE INVENTION

Field of the Invention

The present invention relates to a technology of inspecting an insulating film formed in an inspection sample mainly made of a semiconductor material.

Description of the Background Art

The insulating film (passivation film) is formed on a surface of a semiconductor wafer in order to prevent degradation. In a solar cell, the insulating film (passivation film) is formed in order to provide high conversion efficiency.

C-V (Capacitance-Voltage) measurement is widely performed as a method for evaluating the insulating film formed on the semiconductor wafer. In the C-V measurement, an electrode disc of aluminum is deposited on the insulating film of the semiconductor wafer, and a probe pin is brought into contact with the electrode disc, thereby applying voltage to the semiconductor wafer. A change in electric capacity (capacitance) corresponding to the voltage is measured by changing the voltage.

For example, Patent Document 1 (Japanese Patent Application Laid-Open No. 2013-38340) discloses a technology associated with the C-V measurement of the semiconductor wafer.

In the C-V measurement, complicated work is problematic. That is, for the C-V measurement, it is necessary to bring the probe pin into contact in each electrode disc to measure the electric capacity, which results in the problematic measurement work.

Additionally, for C-V measurement, resolution is hard to be improved. That is, in the C-V measurement, compactness and a small forming interval of the electrode disc deposited on the surface of the insulating film are required to improve the resolution. However, the resolution is hard to be improved from the viewpoint of workability degradation and cost.

SUMMARY OF THE INVENTION

The present invention aims at the inspection apparatus that inspects the insulating film formed on the surface of the inspection sample mainly made of the semiconductor material.

According to a first aspect of the present invention, an inspection apparatus that inspects an insulating film formed on a surface of an inspection sample mainly made of a semiconductor material, the inspection apparatus includes: a retainer that retains the inspection sample; a light irradiator that irradiates the inspection sample with light having a predetermined wavelength to cause the inspection sample to emit a terahertz wave; a detector that detects electric field intensity of the terahertz wave emitted from the inspection sample; and a comparator that compares the electric field intensity of the terahertz wave emitted from the inspection sample to an evaluation reference value. At this point, the evaluation reference value is smaller than an absolute value of a saturation value of the electric field intensity of the terahertz wave, the terahertz wave being generated by irradiating a reference sample, which is a reference of the inspection sample, with the light having the predetermined wavelength while different voltages are applied to the reference sample.

In the inspection apparatus of the first aspect, the surface potential can indirectly be observed from the electric field intensity of the terahertz wave. The surface potential correlates with the fixed charge that is one of capabilities of the insulating film. Therefore, a characteristic of the insulating film can properly be evaluated by comparing whether or not the electric field intensity of the terahertz wave exceeds the evaluation reference value. Even for the inspection sample in which the electrode is not formed, because the terahertz wave can be measured, the insulating film can be inspected with fine resolution. Additionally, because the point to be measured is irradiated with light, the inspection can be facilitated compared with the conventional C-V measurement that is performed while the probe pin contacts the electrode.

According to a second aspect, the inspection apparatus of the first aspect further includes: a voltage application unit that applies voltage to the inspection sample; and a voltage changer that changes the voltage applied from the voltage application unit.

In the inspection apparatus of the second aspect, the terahertz wave is detected while the voltage is applied to the reference sample, so that the saturation value can be specified with the inspection apparatus.

According to a third aspect, an inspection apparatus that inspects an insulating film formed on a surface of an inspection sample mainly made of a semiconductor material, the inspection apparatus includes: a retainer that retains the inspection sample; a light irradiator that irradiates the inspection sample with light having a predetermined wavelength to cause the inspection sample to emit a terahertz wave; a detector that detects electric field intensity of the terahertz wave emitted from the inspection sample; a voltage application unit that applies voltage to the inspection sample; a voltage changer that changes the voltage applied from the voltage application unit; and a voltage specifying unit that specifies an applied voltage at which electric field intensity of the terahertz wave emitted from the inspection sample becomes zero.

In the inspection apparatus of the third aspect, a flat band voltage can easily be acquired by specifying the applied voltage at which the electric field intensity of the terahertz wave becomes zero. In the case that the flat band voltage is acquired by the conventional C-V measurement, it is necessary to derive the flat band voltage by a calculation in which various parameters (such as a thickness or relative permittivity of the insulating film and a surface dope concentration of the semiconductor layer) are used. Accordingly, the flat band voltage can easily and accurately be acquired compared with the conventional C-V measurement.

According to a fourth aspect, the inspection apparatus of the third aspect further includes a converter that converts the electric field intensity of the terahertz wave into the electric capacity based on correspondence information between the electric field intensity of the terahertz wave and an electric capacity.

In the inspection apparatus of the fourth aspect, the inspection equivalent to the C-V measurement can be performed by converting the THz intensity into the electric capacity at each applied voltage.

According to a fifth aspect, the inspection apparatus of the third or fourth aspect further includes a net charge deriver that derives a net charge using the applied voltage specified with the voltage specifying unit.

In the inspection apparatus of the fifth aspect, a fixed voltage exhibiting the capability of the insulating film formed in the inspection sample can be derived by deriving the net charge.

According to a sixth aspect, the inspection apparatus of any one of the third to fifth aspects further includes a scanner that scans the inspection sample with the light having the predetermined wavelength.

In the inspection apparatus of the sixth aspect, the electric field intensity of the terahertz wave emitted at each measurement point is acquired, so that a characteristic of the insulating film formed on the surface of the inspection sample can two-dimensionally be inspected. For example, in-plane uniformity of the insulating film can be evaluated by the two-dimensional inspection.

The present invention also aims at the inspection method for inspecting the insulating film formed on the surface of the inspection sample mainly made of the semiconductor material.

According to a seventh aspect, an inspection method for inspecting an insulating film formed on a surface of an inspection sample mainly made of a semiconductor material, the inspection method includes the steps of: (a) specifying a saturation value of electric field intensity of a terahertz wave, the terahertz wave being generated by irradiating a reference sample, which is a reference of the inspection sample, with light having a predetermined wavelength while different voltages are applied to the reference sample; (b) detecting the electric field intensity of the terahertz wave, which is generated by irradiating the inspection sample with the light having the predetermined wavelength; and (c) comparing the electric field intensity of the terahertz wave detected in the step (b) to an evaluation reference value that is smaller than an absolute value of the saturation value.

In the inspection method of the seventh aspect, the surface potential can indirectly be observed from the electric field intensity of the terahertz wave. The surface potential correlates with the fixed charge that is one of capabilities of the insulating film. Therefore, a characteristic of the insulating film can properly be evaluated by comparing whether or not the electric field intensity of the terahertz wave exceeds the evaluation reference value. Even for the inspection sample in which the electrode is not formed, because the terahertz wave can be measured, the insulating film can be inspected with fine resolution. Additionally, because the point to be measured is irradiated with light, the inspection can be facilitated compared with the conventional C-V measurement that is performed while the probe pin contacts the electrode.

According to an eighth aspect, an inspection method for inspecting an insulating film formed on a surface of an inspection sample mainly made of a semiconductor material, the inspection method includes the steps of: (A) detecting electric field intensity of a terahertz wave, the terahertz wave being generated by irradiating the inspection sample with light having a predetermined wavelength while different voltages are applied to the inspection sample; and (B) specifying an applied voltage at which the electric field intensity of the terahertz wave emitted from the inspection sample becomes zero based on the electric field intensity of the terahertz wave detected in the step (A).

In the inspection method of the eighth aspect, the flat band voltage can easily be acquired by specifying the applied voltage at which the electric field intensity of the terahertz wave becomes zero. In the case that the flat band voltage is acquired by the conventional C-V measurement, it is necessary to derive the flat band voltage by a calculation in which various parameters (such as a thickness or relative permittivity of the insulating film and a surface dope concentration of the semiconductor layer) are used. Accordingly, the flat band voltage can easily and accurately be acquired compared with the conventional C-V measurement.

An object of the present invention is to provide a novel technology of inspecting the insulating film formed in the semiconductor sample.

These and other objects, features, aspects and advantages of the present invention will become more apparent from the following detailed description of the present invention when taken in conjunction with the accompanying drawings.

BRIEF DESCRIPTION OF THE DRAWING

FIG. 4 is a schematic sectional view of a reference sample;

FIG. 11 is a view illustrating a flow for acquiring the correspondence information in the inspection apparatus of the second preferred embodiment.

DESCRIPTION OF THE PREFERRED EMBODIMENTS

Figure 1:
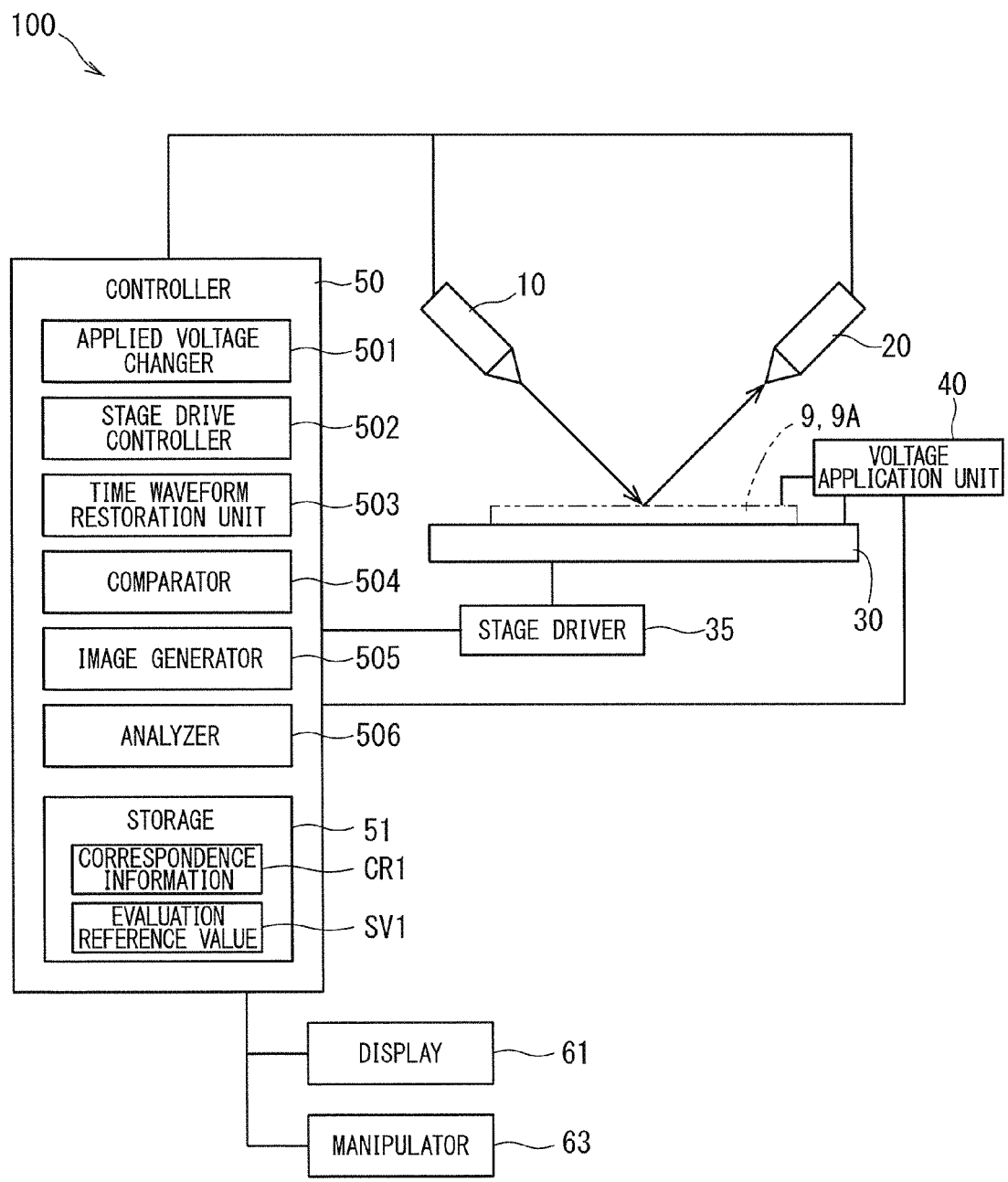
FIG. 1 is a schematic diagram illustrating an entire configuration of an inspection apparatus according to a first preferred embodiment.

Hereinafter, preferred embodiments of the present invention will be described below with reference to the accompanying drawings. The components of the preferred embodiment are described only by way of example, but the present invention is not limited to the preferred embodiment. In the drawings, for the sake of easy understanding, a size of each unit or the number of units is exaggerated or simplified as needed basis.

1. First Preferred Embodiment

Figure 2:
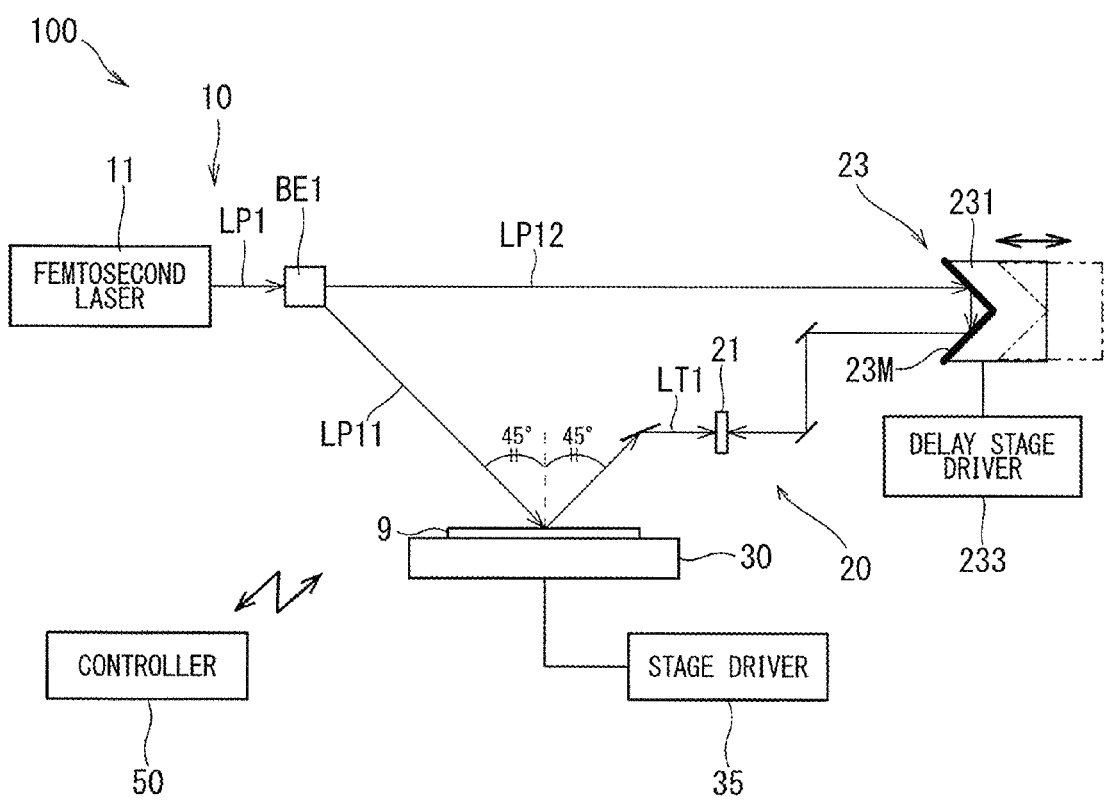
FIG. 2 is a schematic diagram illustrating configurations of a light irradiator and a detector in the inspection apparatus of the first preferred embodiment.
Figure 3:
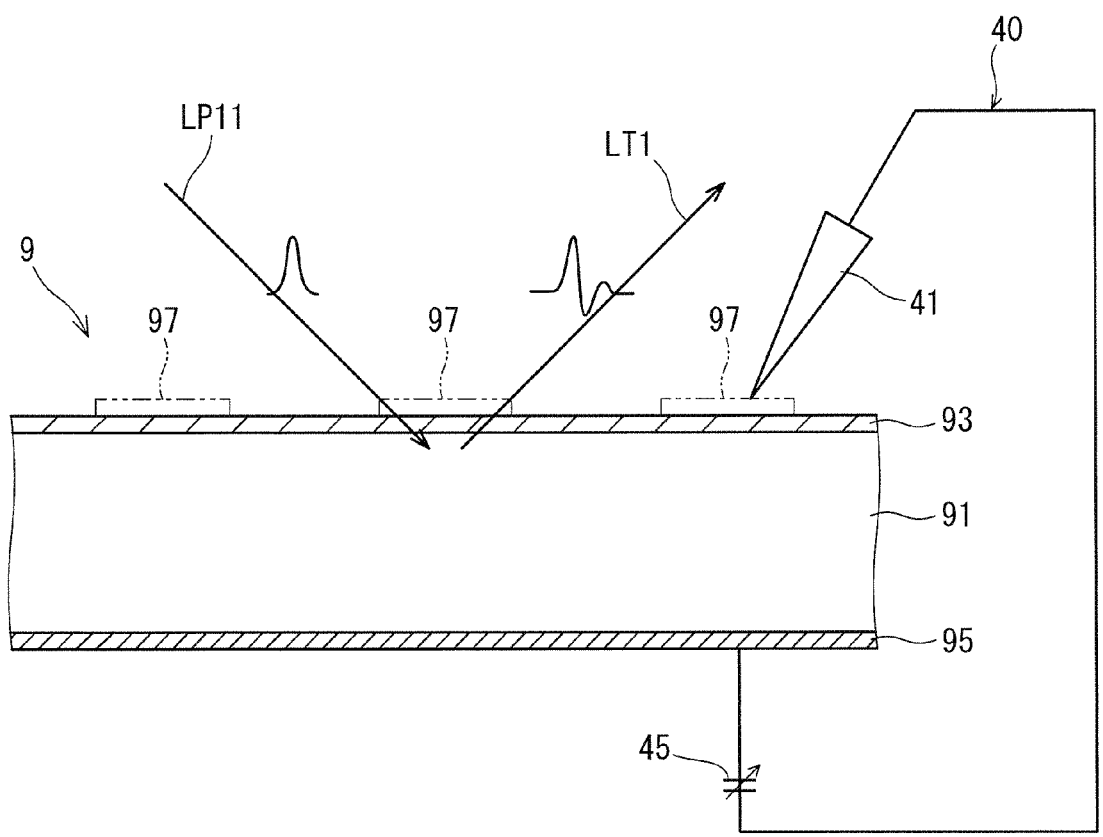
FIG. 3 is a schematic sectional view of an inspection sample.

FIG. 1 is a schematic diagram illustrating an entire configuration of an inspection apparatus 100 according to a first preferred embodiment. FIG. 2 is a schematic diagram illustrating configurations of a light irradiator 10 and a detector 20 of the inspection apparatus 100. FIG. 3 is a schematic sectional view of an inspection sample 9. FIG. 4 is a schematic sectional view of a reference sample 9A.

The inspection apparatus 100 inspects an insulating film on a surface of an inspection sample 9. The inspection sample 9 is a general semiconductor device or photo device. The semiconductor device means various electronic devices such as a transistor and an integrated circuit (IC and LSI) made of the semiconductor of Si, Ge, GaAs, SiC, or GaN and a power device in which a resistor or a capacitor and a wide-gap semiconductor are used. The photo device means electronic devices, such as a photodiode, image sensors such as a CMOS sensor and a CCD sensor, a solar cell, and an LED, in which a semiconductor photoelectric effect is used.

Hereinafter, as illustrated in FIG. 3, it is assumed that the inspection sample 9 includes a semiconductor layer 91, an insulating film 93, and a back electrode 95. It is also assumed that the semiconductor layer 91 is a p-type silicon layer. For example, the insulating film 93 is mainly made of SiOx, SiNx, or AlOx. The insulating film 93 is formed on a principal surface (largest surface) on one of sides of the semiconductor layer 91. The back electrode 95 mainly made of aluminum is formed on a principal surface on the other side of the semiconductor layer 91.

Plural transparent conductive films 97 mainly made of indium tin oxide (ITO) or zinc oxide (ZnO) are dispersedly formed on the principal surface on one of sides of the insulating film 93. However, the transparent conductive film 97 is not necessarily formed in the inspection sample 9. As described later, in the inspection apparatus 100, the insulating film 93 can be inspected even in the inspection sample 9 in which the transparent conductive film 97 is not formed.

In the first preferred embodiment, various parameters (such as correspondence information CR1 described later) are acquired using the reference sample 9A prior to the inspection of the inspection sample 9. As illustrated in FIG. 4, preferably the reference sample 9A has the same configuration as the inspection sample 9. However, the reference sample 9A does not necessarily have the same configuration as the inspection sample 9. For example, a thickness of the insulating film 93 of the reference sample 9A may differ from that of the insulating film 93 of the inspection sample 9. An impurity amount of the semiconductor layer 91 of the reference sample 9A may differ from that of the semiconductor layer 91 of the inspection sample 9.

As illustrated in FIG. 1, the inspection apparatus 100 includes the light irradiator 10, the detector 20, a stage 30, a stage driver 35, a voltage application unit 40, and a controller 50.

<Light Irradiator>

The light irradiator 10 irradiates the inspection sample 9 with light (inspection light LP11) having a predetermined wavelength, which causes the inspection sample 9 to emit a terahertz wave LT1 (electromagnetic wave of 0.1 THz to 30 THz).

As illustrated in FIG. 2, the light irradiator 10 includes a femtosecond laser 11. For example, the femtosecond laser 11 emits pulse light (pulse light LP1) having a wavelength of an ultraviolet region to an infrared region including visible light regions from 200 nm (nanometer) to 2.5 μm (micrometer). Specifically, the femtosecond laser 11 emits the linearly-polarized pulse light having a center wavelength of around 800 nm, periods of several kilohertz to several hundred megahertz, and pulse widths of about 10 femtoseconds to about 150 femtoseconds. Alternatively, the femtosecond laser 11 may emit the pulse light having other wavelength regions (for example, a visible light wavelength such as a blue wavelength (450 nm to 495 nm) and a green wavelength (495 nm to 570 nm), an ultraviolet wavelength (200 nm to 380 nm), and a near infrared wavelength (0.7 μm to 2.5 μm)).

The pulse light LP1 emitted from the femtosecond laser 11 is split into two with a beam splitter BE1. The inspection sample 9 is irradiated with one of the two pieces of split pulse light as inspection light LP11. At this point, the light irradiator 10 irradiates the inspection sample 9 with the inspection light LP11 from the side of the insulating film 93. The inspection sample 9 is irradiated with the inspection light LP11 such that an optical axis of the inspection light LP11 is obliquely incident on the insulating film 93. In the first preferred embodiment, an irradiation angle is set such that an incident angle becomes 45 degrees. However, the incident angle is not limited to 45 degrees, but the incident angle can be properly changed within a range of 0 degree to 90 degrees.

The insulating film 93 is irradiated with the spot-like inspection light LP11. At this point, a spot diameter is set to a range of 1 μm to 10 mm by an optical system (not illustrated). However, the spot diameter is not limited to the range of 1 μm to 10 mm. International Patent Publication No. 2006-093265 described a principle of the generation of the terahertz wave in a semiconductor sample such as the inspection sample 9. That is, a sample is irradiated with femtosecond pulse laser to generate a photoexcitation carrier in the sample. The photoexcitation carrier generated in the sample is accelerated by an electric field or diffusion in the sample to generate a transient current. Specifically, the photoexcitation carrier is accelerated by the electric field on a semiconductor surface to generate the transient current. The terahertz wave is generated by the transient current (transient current effect).

The semiconductor surface differs from an inside of a bulk semiconductor crystal in an energy state. However, in an equilibrium state, because the surface and the inside of the crystal have the same Fermi level, a carrier (electron and hole) moves between the levels of the surface state and the inside of the crystal near the surface. The movement of the carrier bends a band structure to generate a surface potential near the surface. The surface potential accelerates the photoexcitation carrier to generate the terahertz wave.

<Detector>

As illustrated in FIG. 2, the detector 20 includes a terahertz wave detector 21. The terahertz wave LT1 is appropriately condensed with a parabolic mirror, and is incident on the terahertz wave detector 21. For example, the terahertz wave detector 21 includes a photoconductive switch (photoconductive antenna). Detection light LP12 is incident on the terahertz wave detector 21. The detection light LP12 is the other piece of pulse light obtained by splitting the pulse light LP1 with the beam splitter BE1. When the detection light LP12 is incident on the terahertz wave detector 21 while the terahertz wave LT1 is incident on the terahertz wave detector 21, the photoconductive switch instantaneously generates current according to electric field intensity (hereinafter, also referred to as "THz intensity") of the terahertz wave LT1. The current corresponding to the electric field intensity is converted into a digital signal through a lock-in amplifier, an I/V conversion circuit and an A/D conversion circuit (all of which are not illustrated), and appropriately transmitted to the controller 50. Thus, in response to the irradiation with the detection light LP12, the terahertz wave detector 21 detects the electric field intensity (terahertz wave intensity, hereinafter also referred to as "THz intensity") of the terahertz wave LT1 generated in the inspection sample 9. The terahertz wave detector 21 may be constructed with an element different from the photoconductive switch. For example, a Schottky barrier diode or a nonlinear optical crystal can be used as an element that detects the terahertz wave.

As illustrated in FIG. 2, the detector 20 includes a delay unit 23. The delay unit 23 is a delay mechanism that provides a delay to the detection light LP12. The delay unit 23 includes a delay stage 231 and a delay stage driver 233.

The delay stage 231 is provided on an optical path of the detection light LP12. The delay stage 231 is a reflecting mirror 23M, which reflects the detection light LP12 in parallel to the incident direction of the detection light LP12 while shifting the detection light LP12 from the optical axis of the incident detection light LP12. The detection light LP12 reflected from the reflecting mirror 23M is led to the terahertz wave detector 21 through a mirror group provided on the optical path of the detection light LP12.

The delay stage driver 233 linearly reciprocates the delay stage 231 along the optical path of the detection light LP12. Therefore, time necessary for the detection light LP12 to arrive at the terahertz wave detector 21 can be delayed because of a change in optical path length of the detection light LP12. Accordingly, timing at which the terahertz wave detector 21 detects the terahertz wave LT1 can be changed. The terahertz wave LT1 generated in the first preferred embodiment is a pulse wave. Therefore, the THz intensity can be detected in different phases by providing the delay to the detection light LP12.

In the first preferred embodiment, the delay is provided to the detection light LP12. Alternatively, the delay may be provided to the inspection light LP11.

<Stage>

The stage 30 is the retainer that retains the inspection sample 9. The stage 30 includes a retaining surface parallel to a horizontal plane. The stage 30 retains the inspection sample 9 such that the inspection light LP11 is incident on the insulating film 93 of the inspection sample 9 in the retaining plane. Examples of the configuration retaining the inspection sample 9 includes a configuration nipping an edge portion of the inspection sample 9, an adhesive sheet adhering to the surface on the other side of the inspection sample 9, and a configuration sticking to the inspection sample 9 through a suction hole made in the retaining plane. The stage 30 is configured to be able to retain the reference sample 9A similarly to the inspection sample 9.

<Stage Driver>

The stage driver 35 moves the stage 30 in the horizontal plane parallel to a top surface of the stage 30 relative to the light irradiator 10 and the detector 20. Therefore, the inspection apparatus 100 is configured to be able to scan the insulating film 93 of the inspection sample 9 retained on the top surface of the stage 30 with the inspection light LP11. The light irradiator 10, the stage 30, and the stage driver 35 is a scanning mechanism that scans the insulating film 93 of the inspection sample 9 with the inspection light LP11. Alternatively, moving means for moving the light irradiator 10 and the detector 20 in the horizontal plane while moving the stage 30 may be provided instead of the movement of the stage 30. The insulating film 93 of the inspection sample 9 may be scanned with the inspection light LP11 by providing change means (such as a galvano mirror) for changing the optical path of the inspection light LP11.

<Voltage Application Unit>

The voltage application unit 40 includes a probe pin 41, an AC voltage source 43, a variable voltage source 45, and an ammeter 47 (see FIGS. 3 and 4). The voltage application unit 40 is connected to the back electrode 95 of the reference sample 9A, and the probe pin 41 is connected to the transparent conductive film 97 of the reference sample 9A. For example, the voltage application unit 40 is connected to the back electrode 95 while a conductive electrode member (not illustrated) provided in the retaining plane of the stage 30 is interposed between the voltage application unit 40 and the back electrode 95. The voltage application unit 40 connected to the reference sample 9A applies the voltage between the back electrode 95 and the transparent conductive film 97. The current generated in applying the voltage to the reference sample 9A is measured with the ammeter 47 of the voltage application unit 40. Thus, in the inspection apparatus 100, the electric capacity of the reference sample 9A can be measured according to the voltage (C-V measurement).

The voltage applied to the reference sample 9A with that the voltage application unit 40 can be changed based on a control signal from an applied voltage changer 501 of the controller 50 (described later). The voltage application unit 40 can apply the voltage to not only the reference sample 9A but also the inspection sample 9 placed on the stage 30.

<Controller>

The controller 50 is configured to control whole operation of the inspection apparatus 100. The controller 50 includes a configuration (such as a CPU, a ROM, and a RAM) of a general computer. The controller 50 includes a storage 51. The storage 51 may be one, such as a RAM, in which information is temporarily stored. The controller 50 is connected to a display 61 constructed with a liquid crystal display or the like and a manipulator 63 constructed with various input devices such as a keyboard and a mouse.

The CPU of the controller 50 operates according to a predetermined program to act as an applied voltage changer 501, a stage drive controller 502, a time waveform restoration unit 503, a comparator 504, an image generator 505, and an analyzer 506.

The applied voltage changer 501 controls the voltage application unit 40 to change the voltage, which is applied to inspection sample 9 (or reference sample 9A) retained on the stage 30. The applied voltage changer 501 changes the applied voltage based on an operator's input command through the manipulator 63.

The stage drive controller 502 controls the stage driver 35 based on the operator's input command through the manipulator 63. When the operator designates a point (inspection target point) to be inspected on the inspection sample 9 through the manipulator 63, the stage drive controller 502 moves the stage 30 such that the inspection target point is matched with an incident position of the inspection light LP11. When the operator designates a range (inspection target range) to be inspected, the stage drive controller 502 moves the stage 30 such that the inspection target range is scanned with the inspection light LP11.

The time waveform restoration unit 503 restores a time waveform of the terahertz wave LT1 based on the THz intensity detected with the terahertz wave detector 21. Particularly, the time waveform restoration unit 503 operates the delay stage driver 233 to move the delay stage 231, thereby provides the delay to the detection light LP12. Therefore, the time waveform of the terahertz wave LT1 is restored by detecting the electric field intensity in the different phase of the terahertz wave LT1.

The comparator 504 compares the THz intensity to an evaluation reference value SV1 stored in the storage 51. The evaluation reference value SV1 is a value that is set to evaluate whether or not the insulating film 93 of the inspection sample 9 is good, and the evaluation reference value SV1 is set to a value (90% of an absolute value of a saturation value) smaller than saturation values $T_{Sat1}$ and $T_{Sat2}$ of the THz intensity. The saturation value is a maximum value or a minimum value of the terahertz wave LT1 emitted from the reference sample 9A. Specifically, the electric field intensity of the terahertz wave LT1 generated by irradiating the reference sample 9A with the inspection light LP11 is measured while different voltages are applied to the reference sample 9A retained on the stage 30, thereby specifying the saturation values $T_{Sat1}$ and $T_{Sat2}$ of the THz intensity.

The image generator 505 generates an image displayed on the display 61. For example, the image generator 505 generates an electric field intensity distribution image. In the electric field intensity distribution image, a distribution of the electric field intensity of the terahertz wave LT1 is visually expressed by colors or patterns, the inspection target range of the inspection sample 9 being scanned with the inspection light LP11 to generate the electric field intensity of the terahertz wave LT1 at each point.

The analyzer 506 acts as the converter that converts the THz intensity into the electric capacity using the correspondence information CR1, the voltage specifying unit that specifies the applied voltage at which the THz intensity becomes zero in order to acquire the flat band voltage of the inspection sample 9, and the net charge deriver that derives a net charge $Q_{net}$ of the inspection sample 9. Each function will be described in detail later.

<Inspection Technique>

A technique of inspecting the inspection sample 9 with the inspection apparatus 100 will be described below. The inspection apparatus 100 can perform first inspection for the inspection sample 9 in which the transparent conductive film 97 is formed on the insulating film 93 and second inspection for the inspection sample 9 in which the transparent conductive film 97 is not formed on the insulating film 93. The first inspection will be described first, and then the second inspection will be described.

<First Inspection>

The first inspection will be described below. The first inspection is an inspection technique of inspecting the inspection sample 9 in which the transparent conductive film 97 is formed on the insulating film 93.

In the first inspection, the THz intensity is measured (hereinafter, also referred to as "THz measurement") with respect to the inspection sample 9. The THz intensity is converted into the electric capacity based on the correspondence information CR1 previously stored in the storage 51. Therefore, the evaluation equivalent to the C-V measurement can be made with respect to the insulating film 93 of the inspection sample 9.

The correspondence information CR1 is information converting the THz intensity into the electric capacity, and the correspondence information CR1 is acquired using the reference sample 9A that is a reference for the inspection sample 9. A flow for acquiring the correspondence information CR1 will be described first, and then a flow of the inspection for the inspection sample 9 using the correspondence information CR1 will be described.

<Method for Acquiring Correspondence Information CR1>

Figure 5:
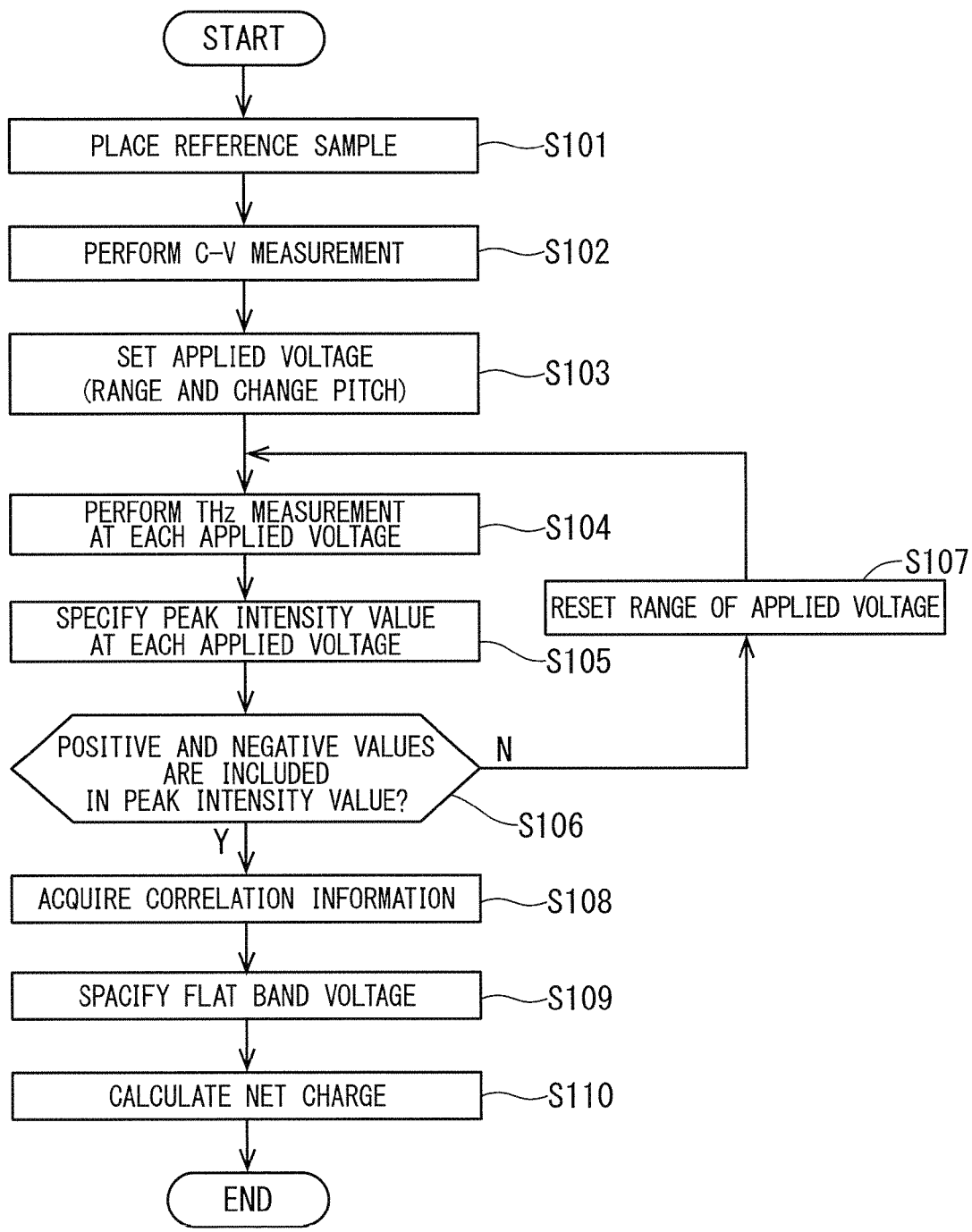
FIG. 5 is a view illustrating a flow for acquiring correspondence information about THz intensity and electric capacity in the inspection apparatus of the first preferred embodiment.

FIG. 5 is a view illustrating a flow for acquiring the correspondence information CR1 about THz intensity and the electric capacity in the inspection apparatus 100.

The reference sample 9A is placed on the stage 30 (step S101). Similarly to the inspection sample 9, the reference sample 9A has a structure in which the insulating film 93 is formed on the surface of the semiconductor layer 91. The transparent conductive film 97 is formed on the insulating film 93 of the reference sample 9A. The transparent conductive film 97 may be formed so as to cover a whole or a part of the insulating film 93.

Then, the C-V measurement is performed using the reference sample 9A (step S102). Particularly, the voltage application unit 40 is connected to the transparent conductive film 97 and the back electrode 95 of the reference sample 9A to measure the current, which is generated according to the applied voltage in a predetermined range (for example, −10 V to +10 V). Therefore, the electric capacity is measured in each of the different applied voltages.

Then, the electric field intensity of the terahertz wave LT1, which is generated at the different voltage, is measured using the reference sample 9A (THz measurement). The voltage applied to the reference sample 9A is set in the THz measurement (step S103). For example, a range (for example, −10 V to +10 V) in which the applied voltage is varied and an interval (a change pitch, for example, every two volts) of the voltage to be changed are set. The setting in step S103 may be performed by the operator based on information input through the manipulator 63 or previously fixed as an initial value.

Then, the THz measurement is performed at each applied voltage (step S104). Particularly, the light irradiator 10 irradiates the reference sample 9A with the inspection light LP11 while the voltage application unit 40 applies each applied voltage, which is set in step S103, to the reference sample 9A. The position where the reference sample 9A is irradiated with the inspection light LP11 is set to the position where the C-V measurement is performed in step S101 (the position of the transparent conductive film 97 on which the probe pin 41 abuts). In step S104, the time waveform restoration unit 503 restores the time waveform of the terahertz wave LT1 generated at each applied voltage.

Figure 7:
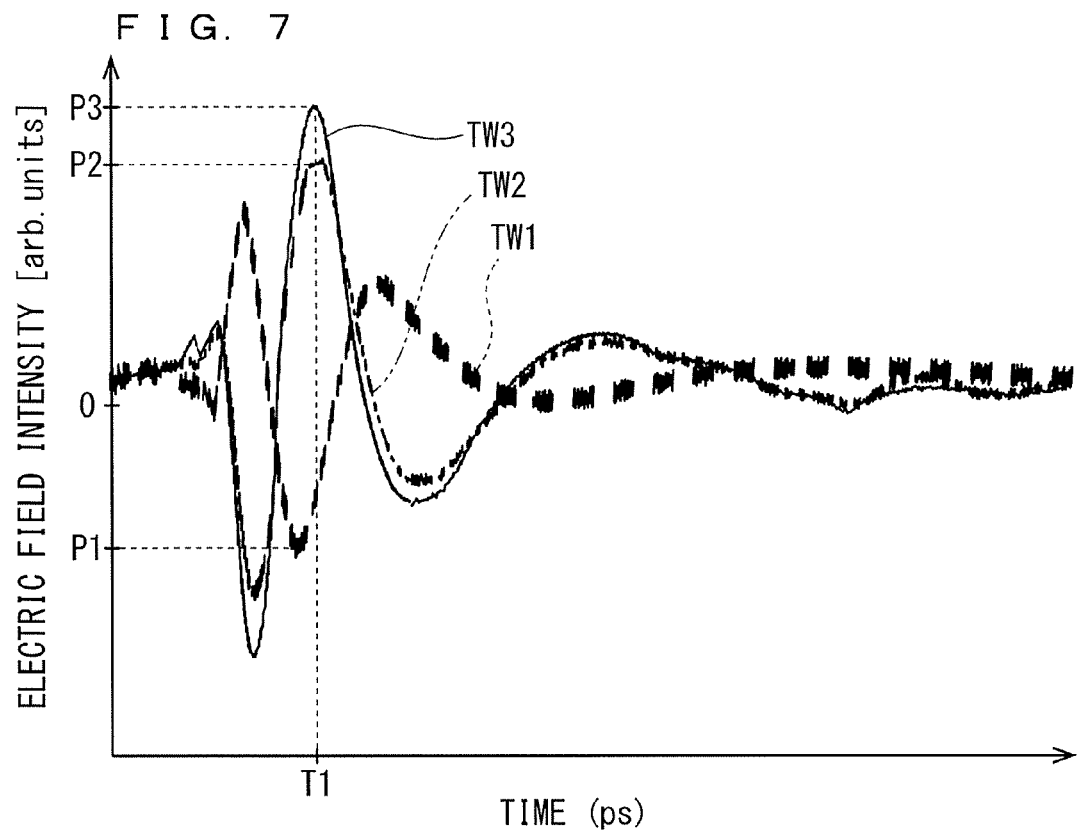
FIG. 7 is a view illustrating a time waveform of a terahertz wave generated at each applied voltage.

FIG. 7 is a view illustrating the time waveform of the terahertz wave LT1 generated at each applied voltage. FIG. 7 illustrates time waveforms TW1, TW2, and TW3 at the applied voltages of −10 V, 0 V, and +10 V, respectively. At this point, the femtosecond laser 11 has laser power of 100 mW. As illustrated in FIG. 7, the waveform of the terahertz wave LT1 is inverted with respect to the electric field intensity by changing the applied voltage. Specifically, in a time waveform TW1 having the applied voltage of −10 V, the electric field intensity deflects from a positive side to a negative side. On the other hand, in time waveforms TW2 and TW3 having the applied voltages of 0 V and 10 V, the electric field intensity deflects from the negative side to the positive side. Amplitude varies when the applied voltage varies.

These THz measurement results reflect a bend of a band structure in the surface of the reference sample 9A. The band structure in the surface is largely bent when the voltage increases, and the THz intensity also increases as the band structure is largely bent. The waveform of the terahertz wave LT1 is inverted at the applied voltages of +10 V and −10 V. This is attributed to the following fact. That is, the band structure of the surface is an inverted layer at the applied voltages of +10 V, and the band structure of the surface is an accumulation layer at the applied voltages of −10 V.

Referring to FIG. 5, when the time waveforms are restored at all the applied voltages, the peak intensity value is specified at each applied voltage (step S105). The peak intensity value means an electric field intensity in which the absolute value is maximized in the time waveform restored at each applied voltage in step S104. For example, as illustrated in FIG. 7, peak intensity values P1, P2, and P3 are obtained in the time waveforms TW1, TW2, and TW3. At this point, P1 is negative and P2 and P3 are positive (P1<0<P2 and P3). P3 is larger than P2 (P2<P3).

A huge amount of measurement time is required to restore the time waveform at all the applied voltages. Therefore, the measurement time may be shortened by the following method. That is, timing of obtaining the peak intensity value is specified from the time waveform restored at a specific applied voltage. The THz measurement at other applied voltages is performed only in the specified timing, and the obtained THz intensity is used as the peak intensity value. In this case, the THz measurement is performed while the delay stage 231 is fixed, so that the measurement time can largely be shortened.

Referring to FIG. 5, when the peak intensity value is specified at each applied voltage, whether or not the positive and negative values are included in the peak intensity value is determined (step S106). When the positive and negative values are not included, the range of the applied voltage is reset (step S107), and the THz measurement is performed at each applied voltage again (step S104). It is not necessary to perform the THz measurement with respect to the applied voltage at which the THz measurement is already performed once.

When the positive and negative values are included in the peak intensity value in step S106, the correspondence information CR1 is obtained (step S108). As described above, the correspondence information CR1 is one that converts the THz intensity into the electric capacity.

Figure 8:
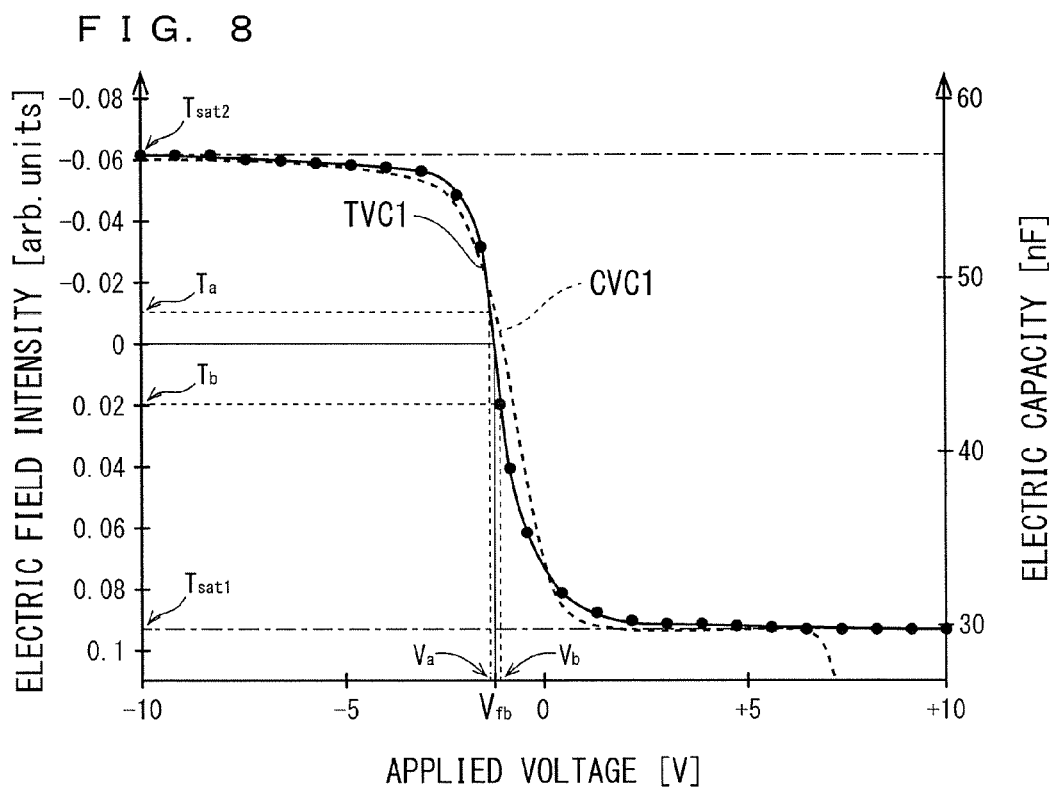
FIG. 8 is a view illustrating a peak intensity value of the THz intensity and the electric capacity at each applied voltage.

FIG. 8 is a view illustrating the peak intensity value of the THz intensity and the electric capacity at each applied voltage. In FIG. 8, a horizontal axis indicates the voltage applied to the reference sample 9A, and a vertical axis indicates the electric field intensity or the electric capacity. In a curve TVC1, plural peak intensity values, which are measured by applying the voltage changed in small steps in the range of −10 V to +10 V, are approximately connected to each other. A curve CVC1 is a C-V curve obtained by performing the C-V measurement (step S102) of the reference sample 9A.

As illustrated in FIG. 8, the curves TVC1 and CVC1 exhibit an extremely similar bend. At each applied voltage, there is an extremely high correlation between the peak intensity value that is the electric field intensity of the terahertz wave LT1 and the electric capacity. Therefore, based on the curves TVC1 and CVC1 obtained using the reference sample 9A, the correspondence information CR1 is acquired in order to convert the THz intensity into the electric capacity. The correspondence information CR1 may be a function (such as a polynomial) or a list of table data in which the voltage corresponds to the electric capacity one to one. The acquired correspondence information CR1 is stored in the storage 51.

Referring to FIG. 5, when the acquisition of the correspondence information CR1 is completed, the flat band voltage of the reference sample 9A is specified (step S109). The flat band voltage means an applied voltage at which a surface potential of the reference sample 9A becomes zero. That is, the flat band voltage corresponds to an applied voltage $V_0$ when the terahertz wave LT1 is not generated. Accordingly, the applied voltage $V_0$ at which the THz intensity becomes zero is specified as the flat band voltage (see FIG. 8).

In the case that the applied voltage $V_0$ at which the THz intensity becomes zero is not included in the THz intensity obtained at each applied voltage in step S105, the applied voltage $V_0$ may be derived by calculation. For example, in a graph of FIG. 8, a minimum value $T_a$ and an applied voltage $V_a$ corresponding to the minimum value $T_a$ in the positive peak intensity value and a maximum value $T_b$ and an applied voltage $V_b$ corresponding to the maximum value $T_b$ in the negative peak intensity value are specified, and connected to each other by a straight lines $(Y=(T_b-T_a) X/(V_b-V_a)-(T_b-T_a) V_a (V_b-V_a)+T_a)$. The applied voltage $V_0$ (that is, a value of X at Y=0) is obtained when the peak intensity value (electric field intensity) becomes zero on the straight line. Thus, the applied voltage $V_0$ at which the THz intensity becomes zero can be specified by the calculation.

The flat band voltage can be derived from the C-V measurement result by a known technique (for example, see Japanese Patent Application Laid-Open No. 2004-111911). Therefore, the flat band voltage may be derived based on the C-V measurement result. The derived value and the flat band voltage obtained based on the THz intensity may be compared to each other. Validity of the flat band voltage obtained from the measurement result of the THz intensity can be evaluated by the comparison. The validity of the evaluation of the insulating film 93 based on the THz measurement can be verified in the reference sample 9A.

In the case that the flat band voltage is obtained from the C-V measurement, it is necessary to make a calculation using various parameters (such as a thickness or relative permittivity of the insulating film 93 and a surface dope concentration of the semiconductor layer 91). On the other hand, the parameter is not required in the case that the flat band voltage is acquired from the THz intensity. For this reason, the flat band voltage can easily and accurately be acquired.

In the case that the reference sample 9A has an irregular surface structure (such as a texture structure of the surface of the solar cell), there is a risk of accurately performing the C-V measurement, which results in a risk of further degrading the accuracy of the flat band voltage. On the other hand, because the light spot diameter is larger than the texture structure, the emission of the terahertz wave LT1 is hardly influenced by the surface structure. For this reason, the flat band voltage can accurately be acquired.

When the flat band voltage is specified, the net charge $Q_{net}$ (total charge) is derived (step S110). The net charge $Q_{net}$ is derived based on the following equation.

$$V_{fb} - \phi_{ms} = \frac{Q_{net}}{C_{OX}}$$

Where $V_{fb}$ is the flat band voltage, $\phi_{ms}$ is the voltage derived from the transparent conductive film 97, and $C_{OX}$ is capacity density derived from the insulating film. $C_{OX}$ corresponds to $\epsilon_s/t$, and is obtained by dividing the maximum value of the capacity measured in the C-V measurement by an electrode area. $\epsilon_s$ is permittivity of the semiconductor layer, t is the thickness of the insulating film, $\phi_{ms}$ is known, and $C_{ox}$ is obtained by the C-V measurement. Therefore, the net charge $Q_{net}$ can be obtained by substituting the flat band voltage $V_{fb}$ specified in step S109.

The net charge $Q_{net}$ can be given by the following equation.

$$Q_{net} = Q_f + Q_{it} + \int_0^t x \rho_{OX} dx$$

Where $Q_f$ is a fixed charge, $Q_{it}$ is a charge derived from an interface state, and a third term is charge density in the insulating film.

Thus, in the inspection apparatus 100, the correspondence information CR1 converting the THz intensity into the electric capacity is acquired using the reference sample 9A that is the reference for the inspection sample 9.

The analyzer 506 may automatically perform in steps S108 to S110, or the operator may perform in steps S108 to S110.

<First Inspection of Inspection Sample>

The inspection apparatus 100 performs the inspection using the correspondence information CR1 about the insulating film 93 formed in the inspection sample 9.

Figure 6:
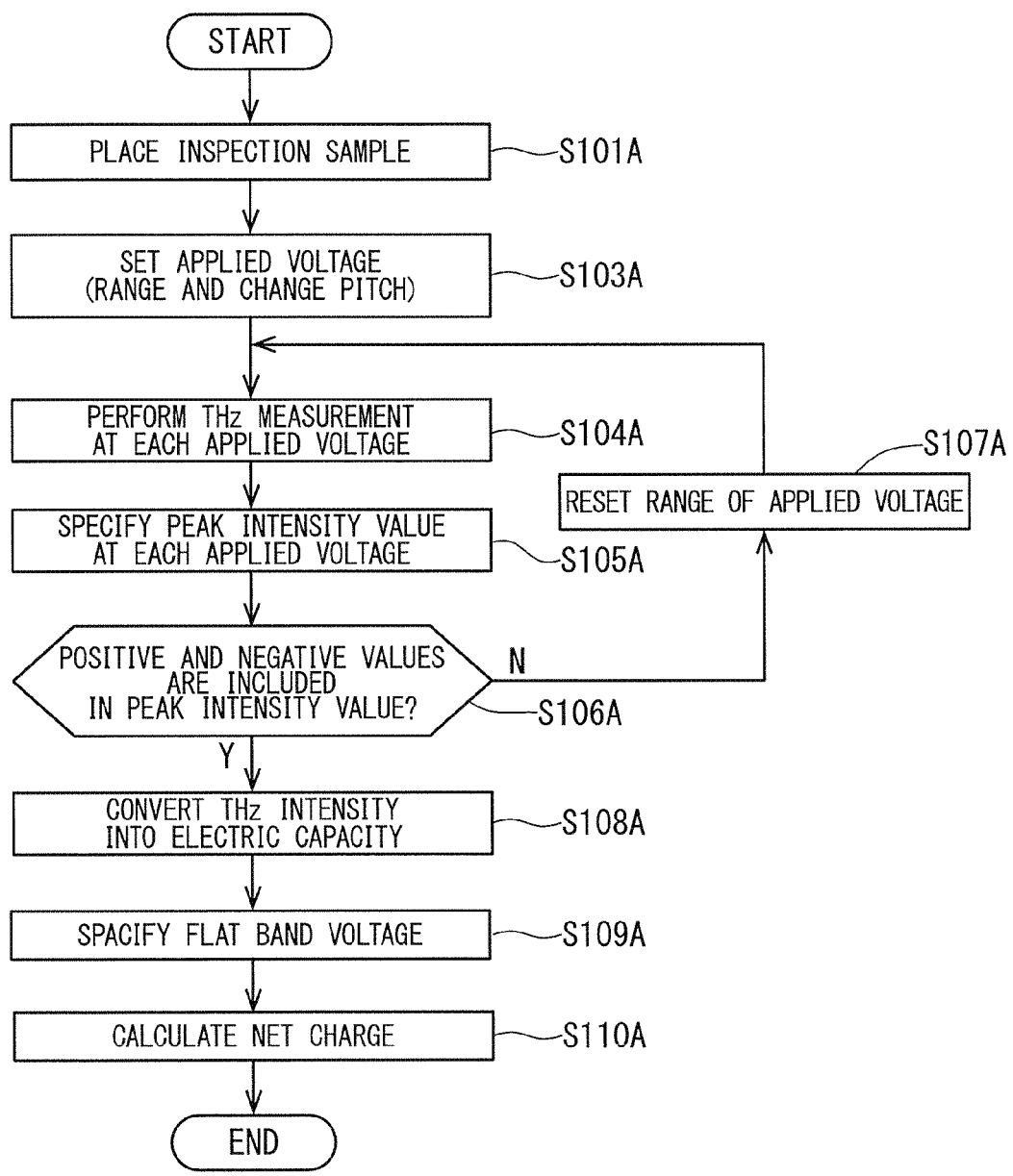
FIG. 6 is a view illustrating a flow of first inspection performed in the inspection apparatus of the first preferred embodiment.

FIG. 6 is a view illustrating a flow of the first inspection performed in the inspection apparatus 100. As illustrated in FIG. 6, the inspection sample 9 is placed on the stage 30 (step S101A). That is, the inspection sample 9 is retained on the stage 30.

The voltage applied to the inspection sample 9 is set (step S103A), the THz intensity is measured at each applied voltage (step S104A), and the peak intensity value is specified at each applied voltage (step S105A). Steps S103A to S105A are similar to steps S103 to S105 of FIG. 5.

Whether or not the positive and negative values are included in the peak intensity value specified in step S105A is determined (step S106A). When the positive and the negative values are not included, the range of the applied voltage is reset (step S107A), and the THz measurement is performed at each applied voltage again (step S104A). It is not necessary to perform the THz measurement with respect to the applied voltage at which the THz measurement is already performed once.

When the positive and negative peak intensity values are included in step S106A, the THz intensity (peak intensity value) is converted into the electric capacity using the correspondence information CR1 (step S108A). Therefore, the information about the THz intensity corresponding to the voltage is converted into the information about the electric capacity corresponding to the voltage.

Then, the flat band voltage and the net charge $Q_{net}$ are acquired (steps S109A and S110A). As described in step S109, the flat band voltage is set to the applied voltage $V_0$ at which the THz intensity becomes zero. The net charge $Q_{net}$ is derived based on the equations described in step S110.

Thus, the electric capacity, the flat band voltage (applied voltage $V_0$), and the net charge $Q_{net}$ (or fixed charge) can be obtained from the THz measurement result. The insulating film 93 in the inspection sample 9 can be evaluated based on these parameters.

The THz measurement result of the inspection sample 9 is graphed similarly to the acquisition of the curve TVC1 in FIG. 8, which allows observation of the band bend of voltage dependence of the insulating film 93. That is, the insulating film 93 of the inspection sample 9 can be evaluated only from the THz intensity obtained in step S105A.

As described above, the flat band voltage can be derived from the electric capacity by the calculation (see Japanese Patent Application Laid-Open No. 2004-111911). The flat band voltage (applied voltage $V_0$) obtained from the THz intensity and the flat band voltage derived from the electric capacity obtained by the conversion of the THz intensity may be compared to each other. Therefore, the validity of the flat band voltage obtained from the THz measurement can be verified. The validity of the evaluation of the insulating film 93 based on the THz measurement can also be verified in the inspection sample 9.

In the case that plural transparent conductive films 97 are formed in the inspection sample 9, the insulating film 93 at each point may be evaluated by performing the THz measurement of each transparent conductive film 97. The in-plane uniformity of the insulating film 93 in the inspection sample 9 can be evaluated by imaging the distribution of the THz intensity (peak intensity value) measured at a specific applied voltage. The distribution of the electric capacity obtained by the conversion of the THz intensity, the distribution of the flat band voltage, and the distribution of the net charge $Q_{net}$ (or fixed charge) may be imaged and displayed on the display 61.

<Second Inspection>

The second inspection will be described below. The inspection sample 9 in which the transparent conductive film 97 is not formed on the insulating film 93 is inspected in the second inspection.

Figure 9:
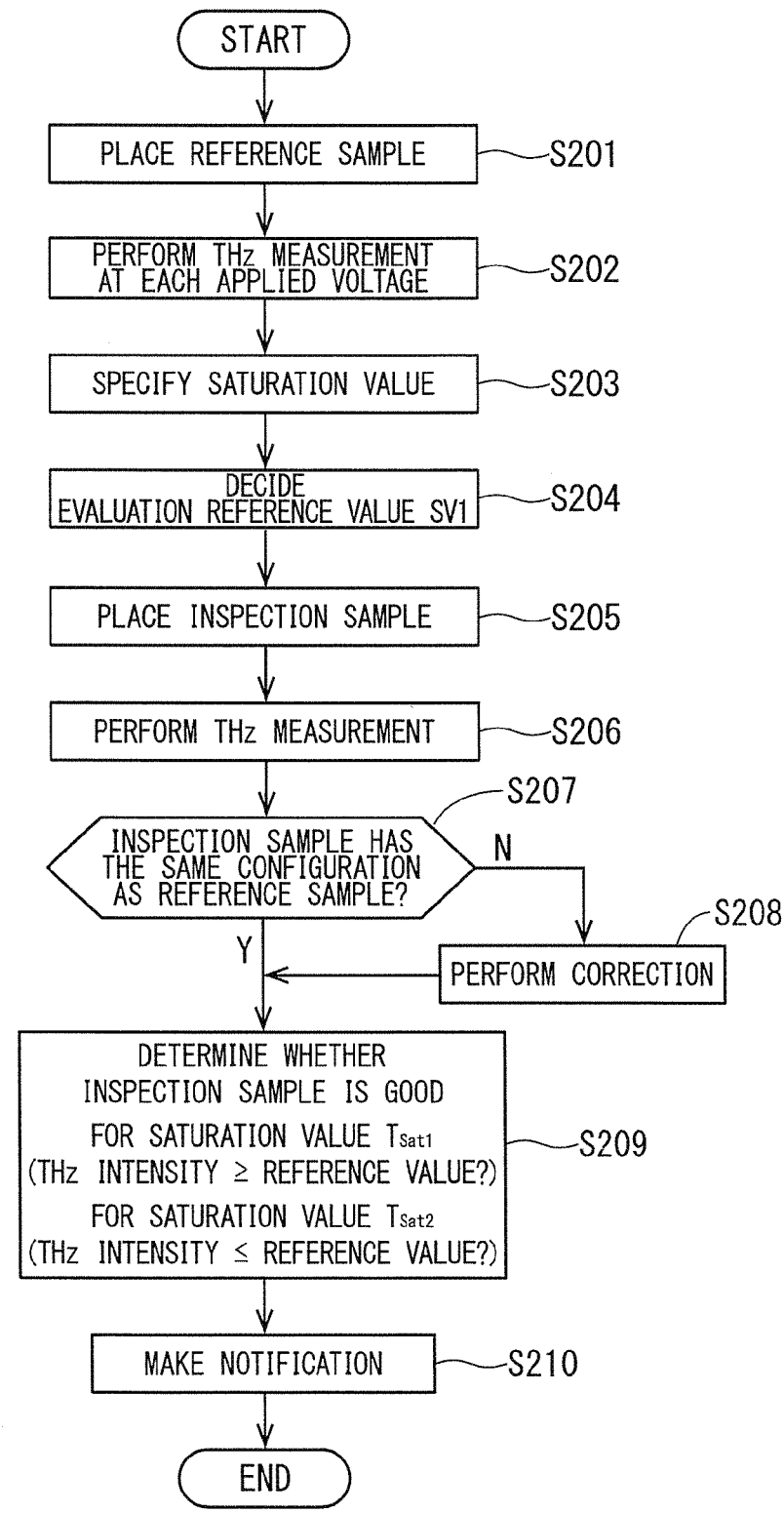
FIG. 9 is a view illustrating a flow of second inspection performed in the inspection apparatus of the first preferred embodiment.

FIG. 9 is a view illustrating a flow of the second inspection performed in the inspection apparatus 100. In the second inspection, the reference sample 9A is placed on the stage 30 (step S201). Step S201 is similar to step S101 of the first inspection.

Then, the THz measurement is performed at plural predetermined applied voltages (step S202). Step S202 is similar to step S104 of the first inspection. In step S202, the time waveform of the terahertz wave LT1 generated at each applied voltage is restored, and the peak intensity value is acquired from the time waveform. As described above, while the delay stage 231 is fixed to a given position, the THz measurement is performed to conveniently acquire the peak intensity value. Therefore, the measurement time may be shortened.

Then, the saturation value of the THz intensity is specified (step S203). Specifically, as illustrated in FIG. 8, the THz intensity (peak intensity value) is gradually saturated as the applied voltage increases in a positive or negative direction. In step S203, saturation values $T_{Sat1}$ (maximum value) and $T_{Sat2}$ (minimum value) of the peak intensity value are specified.

When the saturation values $T_{Sat1}$ and $T_{Sat2}$ are specified, one of the saturation values $T_{Sat1}$ and $T_{Sat2}$ is selected, and the evaluation reference value SV1 is decided based on the selected saturation value $T_{Sat1}$ or $T_{Sat2}$ (step S204). The evaluation reference value SV1 is set to a predetermined ratio (for example, 90%) to the absolute value of the saturation value $T_{Sat1}$ or $T_{Sat2}$. The evaluation reference value SV1 is used in a process (step S209) of evaluating the insulating film 93 of the inspection sample 9.

The evaluation reference value SV1 is decided using the reference sample 9A through steps S201 to S204. The evaluation reference value SV1 is not necessarily acquired with the inspection apparatus 100. For example, the evaluation reference value SV1 may be acquired with an external measurement apparatus.

Then, the inspection sample 9 is placed on the stage 30 (step S205). Therefore, the inspection sample 9 is retained on the stage 30. The THz measurement is performed while the voltage is not externally applied to the inspection sample 9 (step S206). In step S206, the time waveform of the terahertz wave LT1, which is emitted from the inspection sample 9 according to the irradiation of the inspection light LP11, is restored to acquire the peak intensity value.

Whether or not the reference sample 9A in which the evaluation reference value SV1 is acquired and the inspection sample 9 subjected to the THz measurement in step S206 have the same configuration is determined (step S207). Specifically, when the reference sample 9A differs from the inspection sample 9 in a dopant, namely, a p-type or an n-type, or when the reference sample 9A differs from the inspection sample 9 in an impurity doping amount, the THz intensity is corrected according to each difference (step S208).

Whether or not the inspection sample 9 is good is determined based on the THz intensity obtained in step S206 or the corrected THz intensity obtained in step S208 (step S209). Specifically, the comparator 504 compares the THz intensity (or the corrected THz intensity) to the evaluation reference value SV1.

When the THz intensity is greater than or equal to the evaluation reference value SV1 while the saturation value $T_{Sat1}$ is selected in step S204, or when the THz intensity is less than or equal to the evaluation reference value SV1 while the saturation value $T_{Sat2}$ is selected in step S204, it is estimated that the good insulating film 93 is formed in the inspection sample 9. Therefore, the affirmative evaluation is made for the inspection sample 9. On the other hand, when the THz intensity is less than the evaluation reference value SV1 while the saturation value $T_{Sat1}$ is selected in step S204, or when the THz intensity is greater than the evaluation reference value SV1 while the saturation value $T_{Sat2}$ is selected in step S204, possibly the insulating film 93 is defective. Therefore, the negative evaluation is made for the inspection sample 9.

J. Plasma Fusion Res. Vol. 85, No. 12 (2009) 820-824 indicates a relationship between interface fixed charge density in a passivation film (insulating film) formed in a semiconductor sample (crystalline silicon solar cell) and interface recombination speed that is one of values indicating capability of the passivation film (see FIG. 5 of J. Plasma Fusion Res. Vol. 85, No. 12 (2009) 820-824). A simulation shows that the recombination speed is reduced by the bend of the band near the interface (that is, by applying an electric field to a vicinity of the interface). FIG. 5 of J. Plasma Fusion Res. Vol. 85, No. 12 (2009) 820-824 shows that the interface recombination speed is rapidly reduced when a positive or negative fixed charge exceeds a certain value.

As described above, the bend (surface potential) of the band near the interface can indirectly be observed by the THz measurement. The THz intensity increases relatively with increasing surface potential. As the surface potential increases, the fixed charge increases relatively, and the interface recombination speed decreases relatively (that is, the capability of the insulating film 93 is improved). When the THz intensity is sufficiently large, it can be estimated that the interface recombination speed is sufficiently small (that is, the insulating film 93 has the high capability). Therefore, the evaluation reference value SV1 is properly set to determine a magnitude correlation between the evaluation reference value SV1 and the THz intensity, which allows the good evaluation of a characteristic of the insulating film 93 in the inspection sample 9.

When the determination in step S109 is completed, the operator is notified of the determination result (step S210). Specifically, the operator is notified of the determination result so as to be visually able to recognize the determination result through the display 61. Alternatively, the operator may be notified of the determination result by lighting a lamp or making a sound.

As described above, in the second inspection, the capability of the insulating film 93 formed on the surface of the inspection sample 9 can be evaluated based on the THz measurement even in the inspection sample 9 in which the transparent conductive film 97 is not formed.

By scanning a predetermined range of the inspection sample 9 with the inspection light LP11, the THz intensity may be measured at each point to evaluate the insulating film 93 at each point. The distribution of the THz intensity at each point may be imaged. Therefore, the in-plane uniformity of the capability of the insulating film 93 can be evaluated or a defective point can be specified.

In the above description, the second inspection is applied to the inspection sample 9 in which the transparent conductive film 97 is not formed. However, the second inspection can also be applied to the inspection sample 9 in which the transparent conductive film 97 is formed. That is, in the inspection sample 9, the THz measurement is performed at a point where the transparent conductive film 97 is not formed, which allows the evaluation whether or not the insulating film 93 is good.

2. Second Preferred Embodiment

A second preferred embodiment will be described below. Hereinafter, the element having the function similar to that of the already-described element is designated by the same reference numeral or the reference numeral to which an alphabet is added, and sometimes the detailed description is omitted.

Figure 10:
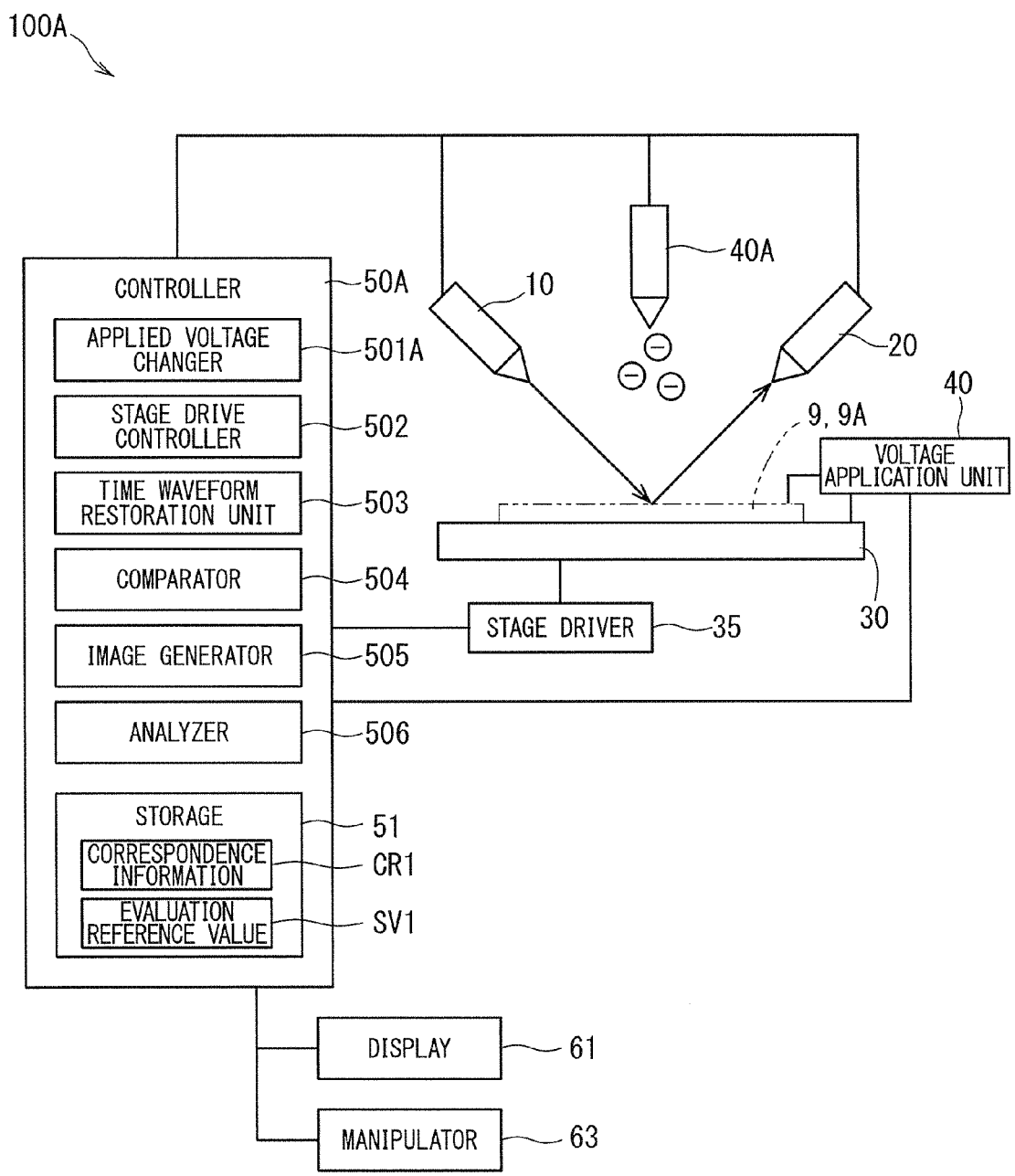
FIG. 10 is a schematic diagram illustrating an entire configuration of an inspection apparatus according to a second preferred embodiment.

FIG. 10 is a schematic diagram illustrating an entire configuration of an inspection apparatus 100A of the second preferred embodiment. The inspection apparatus 100A includes a corona discharger 40A.

The corona discharger 40A emits a positive or negative ion by applying a high voltage to a needle electrode. Therefore, the inspection sample 9 can be charged positive or negative. That is, a pseudo voltage can be applied to the inspection sample 9. An applied voltage changer 501A of a controller 50A controls the corona discharger 40A. The configurations of the inspection apparatus 100A except for the corona discharger 40A are similar to those of the inspection apparatus 100.

<First Inspection>

The first inspection in which the inspection apparatus 100A is used will be described below. A point different from the first inspection performed in the inspection apparatus 100 of the first preferred embodiment will mainly be described below.

FIG. 11 is a view illustrating a flow for acquiring the correspondence information CR1 in the inspection apparatus 100A of the second preferred embodiment. In step S103B corresponding to step S103, a discharge amount of ion emitted from the corona discharger 40A is set with respect to the reference sample 9A. For example, a range in which the discharge amount is changed and an interval (change pitch) of the discharge amount to be changed are set. In step S104B corresponding to step S104, the THz intensity is measured in each discharge amount set in step S103B. In step S105B corresponding to step S105, the peak intensity value is specified in each discharge amount. Therefore, the relationship between the discharge amount and the THz intensity is acquired using the reference sample 9A. In step S107B corresponding to step S107, the range of the discharge amount is reset.

The relationship between the discharge amount and the THz intensity, which is acquired in step S105B, draws a curve similar to the curve TVC1 in FIG. 8. At this point, because the THz intensity and the electric capacity have a high correlation with each other, the discharge amount is approximately converted into the applied voltage based on the relationship between the applied voltage and the electric capacity acquired in step S102 and the relationship between the discharge amount and the THz intensity acquired in step S104B (step S108B). Therefore, the relationship between the discharge amount and the THz intensity can be converted into the relationship between the applied voltage and the THz intensity. The correspondence information CR1 is acquired in order to convert the THz intensity into the electric capacity (step S108B).

Figure 12:
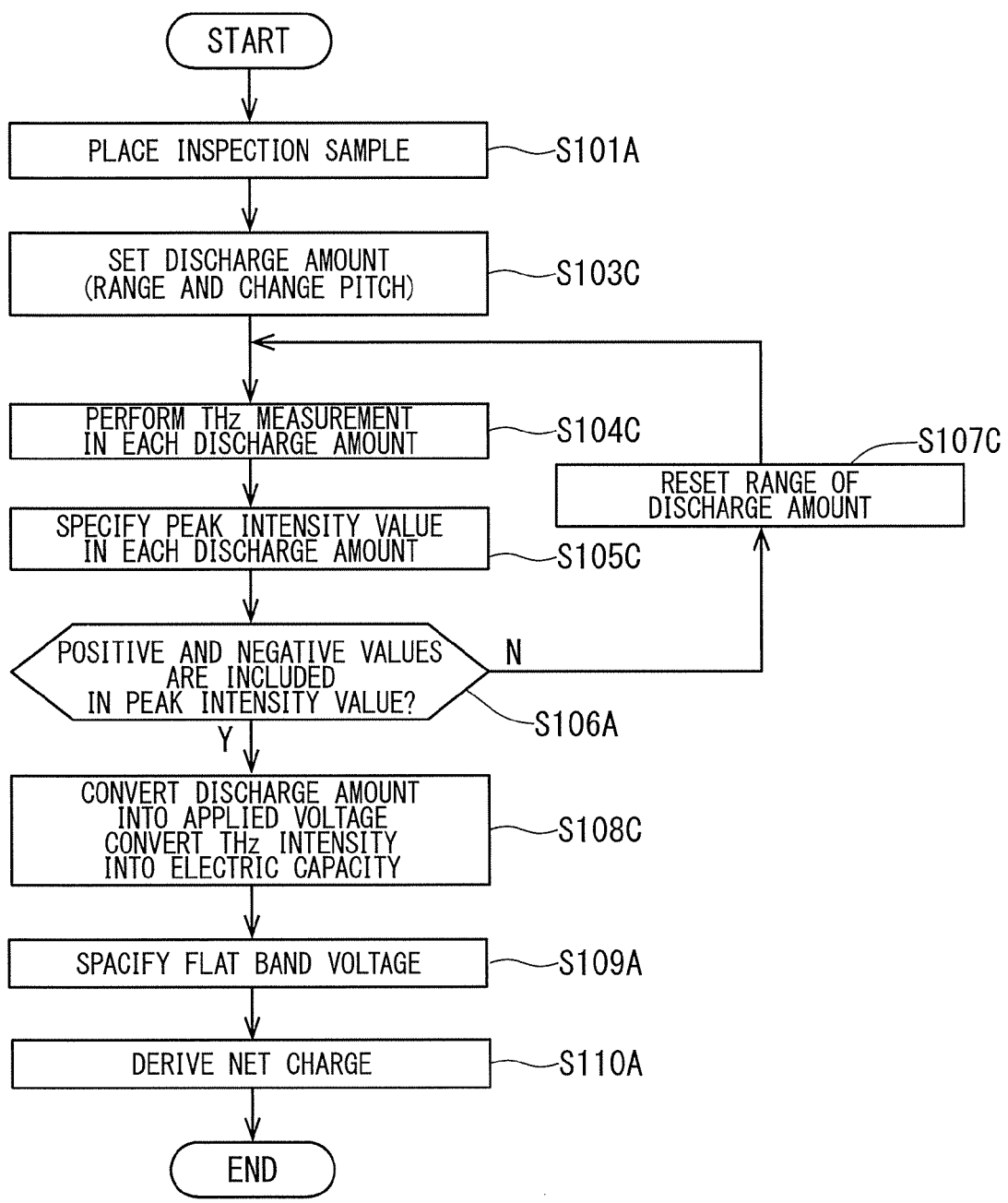
FIG. 12 is a view illustrating a flow of first inspection performed in the inspection apparatus of the second preferred embodiment.

FIG. 12 is a view illustrating a flow of the first inspection performed in the inspection apparatus 100A of the second preferred embodiment. In step S103C corresponding to step S103A, similarly to the step S103B, the discharge amount of ion emitted from the corona discharger 40A is set with respect to the inspection sample 9. In step S104C corresponding to step 104A, the THz measurement is performed in each discharge amount set in step S103C. In step S105C corresponding to step S105A, the peak intensity value is specified in each discharge amount. Therefore, the relationship between the discharge amount and the THz intensity is acquired using the inspection sample 9. In step S107C corresponding to step S107A, the range of the discharge amount is reset.

In step S108C corresponding to step S108A, with respect to the relationship between the discharge amount and the THz intensity acquired in step S105C, the discharge amount is converted into the applied voltage to acquire the relationship between the applied voltage and the THz intensity. The conversion equation used to convert the discharge amount into the applied voltage in step S108B is used in the conversion of step S108C. The THz intensity is converted into the electric capacity using the correspondence information CR1.

Thus, even in the case that the inspection apparatus 100A is used, the first inspection of the inspection sample 9 can be performed.

For the inspection apparatus 100 of the first preferred embodiment, in order to perform the first inspection, it is necessary to form the transparent conductive film 97 and the back electrode 95 to apply the voltage to the inspection sample 9. On the other hand, for the inspection apparatus 100A, the pseudo voltage can be applied in a non-contact manner by the emission of the ion from the corona discharger 40A. Therefore, because the inspection sample 9 in which the transparent conductive film 97 and the back electrode 95 are not formed can be put into the voltage applied state, the first inspection can be performed.

While the invention has been shown and described in detail, the foregoing description is in all aspects illustrative and not restrictive. It is therefore understood that numerous modifications and variations can be devised without departing from the scope of the invention.

What is claimed is:

1. An inspection apparatus that inspects an insulating film formed on a surface of an inspection sample mainly made of a semiconductor material, the inspection apparatus comprising:
    a retainer that retains said inspection sample;
    a light irradiator that irradiates said inspection sample with light having a predetermined wavelength to cause said inspection sample to emit a terahertz wave;
    a detector that detects electric field intensity of said terahertz wave emitted from said inspection sample; and
    a comparator that compares said electric field intensity of said terahertz wave emitted from said inspection sample to an evaluation reference value,
    wherein said evaluation reference value is smaller than an absolute value of a saturation value of said electric field intensity of said terahertz wave, said terahertz wave being generated by irradiating a reference sample, which is a reference of the inspection sample, with said light having said predetermined wavelength while different voltages are applied to said reference sample.

2. The inspection apparatus according to claim 1, further comprising:
    a voltage application unit that applies voltage to said inspection sample; and
    a voltage changer that changes the voltage applied from said voltage application unit.

3. An inspection apparatus that inspects an insulating film formed on a surface of an inspection sample mainly made of a semiconductor material, the inspection apparatus comprising:
    a retainer that retains said inspection sample;
    a light irradiator that irradiates said inspection sample with light having a predetermined wavelength to cause said inspection sample to emit a terahertz wave;
    a detector that detects electric field intensity of said terahertz wave emitted from said inspection sample;
    a voltage application unit that applies voltage to said inspection sample;
    a voltage changer that changes the voltage applied from said voltage application unit; and
    a voltage specifying unit that specifies an applied voltage at which said electric field intensity of said terahertz wave emitted from said inspection sample becomes zero.

4. The inspection apparatus according to claim 3, further comprising a converter that converts said electric field intensity of said terahertz wave into electric capacity based on correspondence information between said electric field intensity of said terahertz wave and an electric capacity.

5. The inspection apparatus according to claim 3, further comprising a net charge deriver that derives a net charge using said applied voltage specified with said voltage specifying unit.

6. The inspection apparatus according to claim 3, further comprising a scanner that scans said inspection sample with said light having said predetermined wavelength.

7. An inspection method for inspecting an insulating film formed on a surface of an inspection sample mainly made of a semiconductor material, the inspection method comprising steps of:
    (a) specifying a saturation value of electric field intensity of a terahertz wave, said terahertz wave being generated by irradiating a reference sample, which is a reference of the inspection sample, with light having a predetermined wavelength while different voltages are applied to said reference sample;
    (b) detecting said electric field intensity of said terahertz wave, which is generated by irradiating said inspection sample with said light having said predetermined wavelength; and
    (c) comparing said electric field intensity of said terahertz wave detected in said step (b) to an evaluation reference value that is smaller than an absolute value of said saturation value.

8. An inspection method for inspecting an insulating film formed on a surface of an inspection sample mainly made of a semiconductor material, the inspection method comprising steps of:
    (A) detecting electric field intensity of a terahertz wave, said terahertz wave being generated by irradiating said inspection sample with light having a predetermined wavelength while different voltages are applied to said inspection sample; and (B) specifying an applied voltage at which said electric field intensity of said terahertz wave emitted from said inspection sample becomes zero based on said electric field intensity of said terahertz wave detected in said step (A).

* * * * *